(12) United States Patent
Del Bigio et al.

(10) Patent No.: US 8,012,116 B2
(45) Date of Patent: Sep. 6, 2011

(54) DEVICE TO REDUCE BRAIN EDEMA BY SURFACE DIALYSIS AND COOLING

(76) Inventors: Marc Ronald Del Bigio, Winnipeg (CA); Alexander Viktor Shulyakov, Winnipeg (CA)

( * ) Notice: Subject to any disclaimer, the term of this patent is extended or adjusted under 35 U.S.C. 154(b) by 487 days.

(21) Appl. No.: 12/193,133

(22) Filed: Aug. 18, 2008

(65) Prior Publication Data

US 2009/0048582 A1 Feb. 19, 2009

Related U.S. Application Data

(60) Provisional application No. 60/956,424, filed on Aug. 17, 2007.

(51) Int. Cl.
*A61M 37/00* (2006.01)
*C02F 1/44* (2006.01)

(52) U.S. Cl. ............... 604/9; 604/6.13; 604/7; 210/645; 210/649; 210/652

(58) Field of Classification Search ................ 604/7–10, 604/540, 27, 6.13; 210/645, 649, 651
See application file for complete search history.

(56) References Cited

U.S. PATENT DOCUMENTS

| | | | | |
|---|---|---|---|---|
| 4,840,617 A | * | 6/1989 | Osterholm | 604/174 |
| 6,537,241 B1 | * | 3/2003 | Odland | 604/9 |
| 6,709,426 B2 | * | 3/2004 | Gijsbers et al. | 604/500 |
| 2006/0073098 A1 | * | 4/2006 | Wang | 424/9.1 |

* cited by examiner

*Primary Examiner* — Leslie Deak
(74) *Attorney, Agent, or Firm* — Michael R. Williams; Ade & Company

(57) ABSTRACT

We have developed a novel method of brain surface dialysis that reduces intracranial pressure and modifies movement of extracellular fluid in a rat model of brain injury. A chamber with a semipermeable membrane at the site of brain contact is perfused with a hyperosmolar solution (e.g. 15% dextran, inulin, hydroxyethyl starch). It is also capable of providing local brain cooling. In principle, osmotic forces draw water and small molecules from the injured brain into the dialysis chamber thereby reducing brain swelling. The dialysate does not move into the brain.

4 Claims, 7 Drawing Sheets

DEVICE TO REDUCE BRAIN EDEMA BY SURFACE DIALYSIS AND COOLING

PRIOR APPLICATION INFORMATION

The instant application claims the benefit of U.S. Provisional Patent Application 60/956,424, filed Aug. 17, 2007.

BACKGROUND OF THE INVENTION

Brain edema is an accumulation of water within the brain tissue. It is a frequent complication after brain damage (stroke or injury)[31]. Edema tends to be maximal at approximately 2 days after injury, and can persist as long as one week. Edema causes the brain to swell, and when the brain swells, pressure inside the head rises and causes further permanent damage or potentially leads to death. Intravenous administration of drugs (e.g. mannitol or other osmotic agents) can dehydrate the uninjured parts of brain to temporarily relieve pressure. Unfortunately, this approach is limited because the osmotic agents enter damaged brain through leaking blood vessels and the swelling in these regions becomes worse ("rebound" phenomenon)[25]. In desperation, surgeons can remove the skull that overlies the damaged brain to allow the brain to swell outward[21]. Experimentally, cooling the brain from the normal 37° C. to ~32° C. can be protective, but clinically local cooling of damaged brain is difficult and cooling of the entire body can have serious side effects (e.g. infection, bleeding). Therefore, there is no effective clinical treatment for severe cases of brain edema.

Interstitial fluid (ISF), also referred to as extracellular fluid, moves through brain by diffusion among cells and by bulk flow especially alongside blood vessels[1]. The predominant flow is toward the ventricular cavities in the center of the brain, where it contributes to cerebrospinal fluid (CSF) formation. The pia mater/glia limitans on the outer surface of the brain may act as a physical barrier and regulatory interface between the extracellular compartment of the brain and the CSF in the subarachnoid space, which surrounds the brain[11]. The arachnoid is a thin tissue layer that contains the CSF around the brain and serves as a barrier against the bulk movement of fluids and large molecular weight substances[2]. The arachnoid is in intimate contact with, but not attached to, the dura mater, which is a tough fibrous layer that is adherent to the inner surface of the skull. Electrophysiological and tracer studies show that exchange of small molecules can occur across the pia, arachnoid, and even the thin dura of small animals[3,29,30,35,43,54].

As discussed above, brain edema is an accumulation of water within the brain parenchyma. It is a universal physiological reaction to brain damage. The localization of edema fluid depends on the etiology of brain damage, and is defined by accumulation in extracellular ("vasogenic"; i.e. due to leaking blood vessels) or intracellular (also called "cytotoxic"; i.e. due to cell swelling when function of the cell membrane fails from exposure to disturbed environment or when energy supplies such as oxygen and glucose are lacking) compartments, potentially in combination. Water and fluid retention can be aggravated by the presence of small molecules that leak through damaged blood vessels and from damaged cells into the extracellular space. Here they can act as osmotic agents that prevent the free flow of water. Edema contributes to brain swelling and elevated intracranial pressure (ICP)[27,51]. As discussed above, there remains no effective clinical treatment for severe cases[37], despite availability of hyperosmolar agents[5,53], barbiturates[42], physiologic support[38], external ventricular drainage, and hemicraniectomy[32,44].

Physical processes such as osmosis and diffusion facilitate the transport of water and dissolved small molecules from solutions through membranes. Dialysis is defined as the process of separating crystalloids (ions and other small molecules dissolved in a liquid) and colloids (large molecules, e.g. proteins, dissolved or suspended in a liquid) in solution by the difference in their rates of diffusion across a semipermeable membrane. This principle is in use for therapeutic hemodialysis (i.e. cleansing of the blood in the case of kidney failure)[15] and extracellular fluid sampling by intraparenchymal brain microdialysis (wherein a small semipermeable catheter filled with a hyperosmotic solution is introduced into the tissue; water and small molecules are drawn into the catheter)[20]. In experimental studies on injured rat brain, edema was reduced when negative hydrostatic pressure was applied for 24 hours to ultra-thin small diameter cuprophan tubes implanted into injury site[48,49].

SUMMARY OF THE INVENTION

According to a first aspect of the invention, there is provided a method of treating brain swelling comprising:
  inserting an osmotic cell into a dural opening or under a dural flap onto a brain that has suffered or is suspected of having suffered an injurious event sufficient to induce swelling, said osmotic cell comprising:
    an osmotic cell body comprising an inner chamber for retaining a solution therein;
    a semi-permeable membrane for contacting the brain;
    an inflow port; and
    an outflow port; and
  flowing a solution having an osmolarity greater than that of fluid in the extracellular compartment of the brain through the inflow port, into the inner chamber, past the semi-permeable membrane and out of the inner chamber through the outflow port such that interstitial fluid from the brain proximal to the semi-permeable membrane osmotically flows across the membrane and into the inner chamber of the body. The temperature of the solution can be controlled in such a way that the surface of the brain can be cooled to a desired temperature. The osmotic cell can be fitted with a temperature monitoring device.

According to a second aspect of the invention, there is provided a device for treating brain swelling comprising:
  an osmotic cell body comprising an inner chamber for retaining a solution therein;
  a semi-permeable membrane arranged for contacting a dural opening or arranged for insertion under a dural flap onto a brain that has suffered or is suspected of having suffered an injurious event sufficient to induce swelling;
  an inflow port for receiving the solution from a reservoir; and
  an outflow port for removal of the solution from the inner chamber.

DESCRIPTION OF THE PREFERRED EMBODIMENTS

Figure 1:
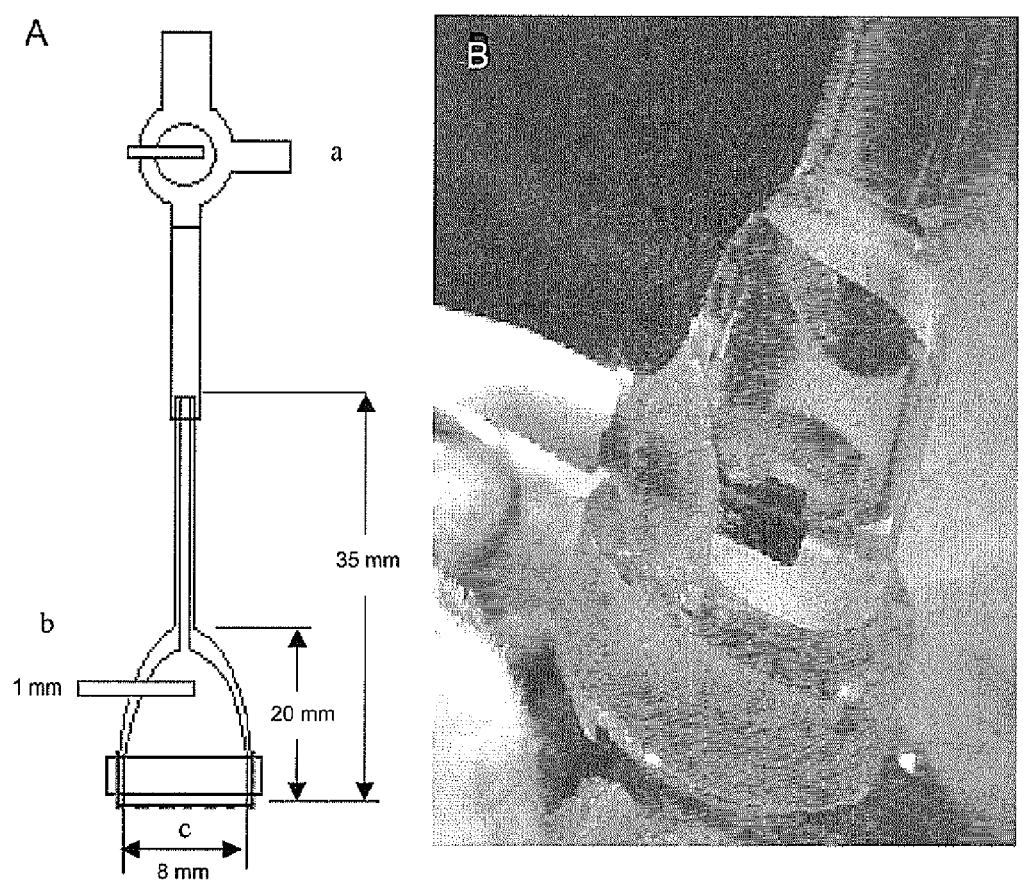
FIG. 1. Schematic diagram (A) showing an experimental osmotic flow cell with inflow (a) and outflow (b) ports and semipermeable membrane at the base (c). Photograph (B) showing the experimental osmotic cell.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

It is shown herein that osmotic dialysis gradients across semipermeable membranes applied to the surface of injured brain can promote ISF transport out of the brain, and protect the damaged brain from ICP elevation. We further show that cooling of the dialysate fluid can cool the brain locally, thereby offering the potential for hypothermic protection[8,9].

In one embodiment of the invention, there is provided a method of treating brain swelling comprising:
  inserting an osmotic cell into a dural opening or under a dural flap onto a brain that has suffered or is suspected of having suffered an injurious event sufficient to induce swelling, said osmotic cell comprising:
    an osmotic cell body comprising an inner chamber for retaining a solution therein;
    a semi-permeable membrane for contacting the brain;
    an inflow port; and
    an outflow port; and
  flowing a solution having an osmolarity greater than that of fluid in the extracellular compartment of the brain through the inflow port, into the inner chamber, past the semi-permeable membrane and out of the inner chamber through the outflow port such that interstitial fluid from the brain proximal to the semi-permeable membrane osmotically flows across the membrane and into the inner chamber of the body.

In another embodiment of the invention, there is provided a device for treating brain swelling comprising:
  an osmotic cell body comprising an inner chamber for retaining a solution therein;
  a semi-permeable membrane arranged for contacting a dural opening or arranged for insertion under a dural flap of a brain that has suffered or is suspected of having suffered a traumatic event sufficient to induce swelling,
  an inflow port for receiving the solution from a reservoir; and
  an outflow port for removal of the solution from the inner chamber.

As will be appreciated by one of skill in the art, a variety of hyperosmolar solutions can be used in the invention. The molecular size of the osmotic agent should exceed the "pore diameter" of the dialysis membrane so that it does not move across the membrane and enter the brain tissue. The solution concentration should be sufficient so that the osmolality exceeds that in the extracellular compartment of the damaged brain, which experimentally has been shown to approach 350-400 mOsm/L $H_2O$[26]. Our studies have shown clearly that colloidal dextran (i.e. glucose polymer) with molecular weight 15,000-20,000 D dissolved (15% W/V) in "artificial cerebrospinal fluid" (final ion concentration in mM: Na 150; K 3.0; Ca 1.4; Mg 0.8; P 1.0; Cl 155) satisfies these conditions (osmolality 392±3 mOsm/L $H_2O$). Other carrier solutions (e.g. 0.9% sodium chloride, Ringers lactate solution, etc.) would also be acceptable. Other osmotic agents could be used e.g. dextrans of other sizes (1500-500000 MW), inulin (5000 MW), dextrin (starch sugar), pentastarch (average MW 265,000 D), or other forms of hydroxyethyl starch. Small molecules such as glucose (180 MW) and mannitol (182 MW) are osmotic agents used for hemodialysis and patient resuscitation. Experiments in the rat model suggest that the osmolarity is very important. A 10% solution of inulin (368 mOsm/L) seems to work, while a 10% solution of pentastarch (338 mOsm/L) seems not to work in pilot experiments.

Physical stability (to avoid leaking or breakage), flexibility (to allow gentle contact with brain surface), and pore diameter (which dictates the dialysate used and the rate of fluid movement) are important factors in construction of the surface dialysis membrane. The effective pore diameter is a function of the molecular makeup of the membranes, which determines how large the spaces are between the molecules. In experimental usage, dialysis membranes from regenerated cellulose (a polymer of cellobiose, a natural plant saccharide) with pore size of 7000 D or 3500 D work. In the short term, they do not have adverse effects on the brain tissue. Cellulose with chemical modifications (e.g. tertiary amine substitution, Hemophan; benzyl substitution, SMC; vitamin E modified; cuprophan; and the like) and synthetic membranes (e.g. polycarbonate/polyether, polysulfone, polymethylmethacrylate, and the like) are available for hemodialysis and could also be used in this application. The chemical composition of the semipermeable membrane is likely less critical than in hemodialysis usage, because there is no contact with flowing blood and therefore activation of blood clotting and complement systems is not important. Nevertheless, chemical modifications alter the mechanical properties and the permeability. Water permeability of hemodialysis membranes is measured as an ultrafiltration coefficient ($K_{UF}$ ml/hr/mmHg). It is dependent on the pore size, the hydrophobic characteristics, and the thickness. Furthermore, the membranes for surface use are in some embodiments preferably thin (<50 μm) to ensure flexibility.

Figure 7:
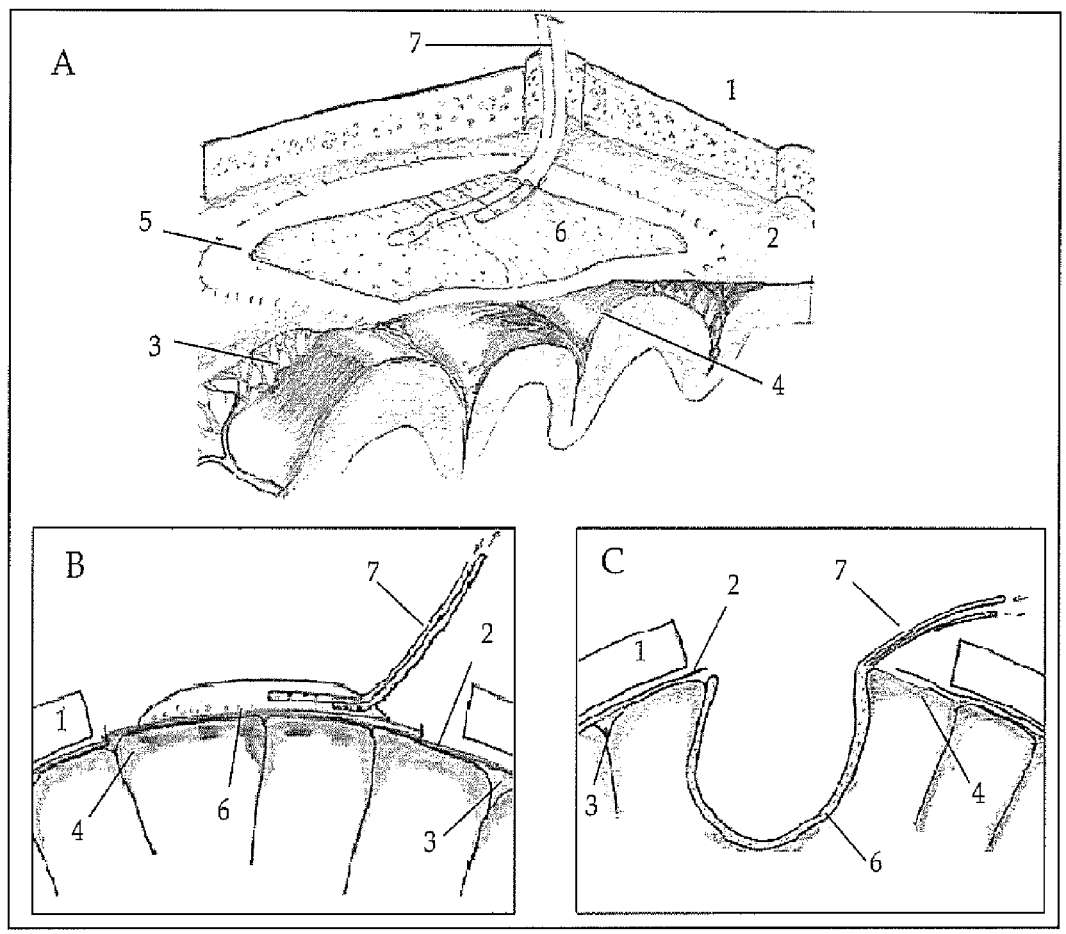
FIG. 7. Surface (A) and cutaway side view (B, C) diagrams showing the osmotic dialysis cell, as it is conceived for use in humans, placed on the brain surface after craniotomy (1—skull) and opening of the dura mater (2). Depending on the nature of the damage, the arachnoid membrane (3) and brain cortex (4) could be intact (B) or disrupted (C). The osmotic cell is placed in the dural opening (5), or potentially under a dural flap, with the semipermeable membrane surface (6) applied to the damaged brain. The osmotic cell is composed of an outer flexible non-permeable material fused to an inner semipermeable membrane. The chamber is flooded with a sterile dialysate that is continually replenished through inflow and outflow tubing (7). Through osmotic forces, excess water and small molecules are drawn from the surface of the brain into the osmotic chamber, thereby preventing brain swelling.

As will be appreciated by one of skill in the art, a surface dialysis device for human use would need to be larger, would need to be flexible to conform to the curved surface of the brain, would need to be sterilizable, and would need to be available in a range of sizes and shapes (round, oval, rectangular) according to the area of brain damaged. In one embodiment, the device comprises a flexible semipermeable membrane fused along the periphery to a flexible impermeable (transparent or opaque) membrane (e.g. silicone, polyvinyl chloride, and the like), which together define the inner chamber of the osmotic cell body as discussed above. In between would be a hollow space or inner chamber with inflow and outflow ports, which may be connected to a tubing system, such as that used for intravenous fluid delivery. The device would be applied to the surface of the damaged brain after opening the skull (by craniotomy) and the dura (see FIG. 7). The device may be held in place by pressure from the scalp, which would be closed over the device leaving only the inflow and outflow tubing exiting from the patient. Sutures may be used to anchor the device or its tubing in place. Sterility would be maintained at these sites in the same manner used for other externalized intracranial devices such as intraventricular drainage catheters or pressure monitors. In some embodiments, the device is equipped with pressure and temperature sensors embedded in or near the surface that contacts the brain. The inflow and outflow ports may be positioned at opposite ends of the device or at the same site running in parallel. Both the inflow and outflow ports may have shutoff valve and connector systems to allow replacement of the reservoirs. The inflow port may be connected to a reservoir of dialysis fluid, which could be cooled to the desired temperature by running a length of the tubing through an ice bath. The outflow port may be connected to a sealed waste reservoir. Flow through the system could be regulated by a gravity drip system or with a mechanical pumping system.

The device will be used for treatment of localized brain swelling, for example that which occurs after mechanical trauma (e.g. head injury) or vascular rupture or occlusion (e.g. stroke). Brain swelling/edema (with or without associated bleeding into brain tissue) that would be treated by this device would be confined to one side or a defined region of the brain (identifiable by imaging modalities such as computed tomographic scanning or magnetic resonance imaging) and would be clinically significant as judged by uncontrollable intracranial pressure and/or deterioration of the patient's neurologic status, despite use of conventional medical and physiologic therapies. Continuous use for 1-5 days, the period of maximal brain swelling, may be necessary in some instances.

In some embodiments, small molecular size drugs (i.e. smaller than the pore size of the dialysis membrane) could be added to the dialysis fluid. They would pass through the membrane by diffusion along the concentration gradient into the brain where they could act locally, not dependent on vascular delivery. These could include antibiotics for treatment of infection, or drugs with neuroprotective or neuroregenerative properties. This includes a wide range of agents exemplified by but not restricted to the following; multifunctional drugs such as minocycline (MW 493), excitatory receptor antagonists such as MK801 (MW 337) which have significant toxicity when administered systemically, adenosine receptor stimulants such as caffeine (MW 194), inhibitors of cell death and apoptosis such as bongkrekic acid (MW 486), small peptides for blocking or stimulating cellular processes, anticonvulsants such as phenytoin (MW 252), and the like.

As will be apparent to one of skill in the art, such a device can also be used for treatment of local swelling in other injured organs or tissues, such as muscle.

As described herein, we have developed a novel method of brain surface dialysis that reduces intracranial pressure and modifies movement of extracellular fluid in a rat model of brain injury. A chamber with a semipermeable membrane at the site of brain contact is perfused with a hyperosmolar solution (e.g. 15% dextran, inulin, hydroxyethyl starch). It is also capable of providing local brain cooling. In principle, osmotic forces draw water and small molecules from the injured brain into the dialysis chamber thereby reducing brain swelling. The dialysate does not move into the brain.

In experimental studies on rats, brain surface dialysis reduced CSF pressure (and presumably intracranial pressure) and was associated with reduced intracerebral spread of Evan's blue-albumin, suggesting that the bulk movement of edema fluid into brain was reduced. The movement of edema fluid from the site of experimental brain injury toward the cerebral ventricles[40] or to local blood vessels[19] for reabsorption is a well-documented phenomenon. In the cryo-injury model, increased water content is detected within 1 hour[45], and reaches a peak at 1 day in rats[22,45] and 5 days in monkeys[41]. Extracellular fluid movement occurs at a rate of up to ~1 mm/minute along a subtle interstitial pressure gradient[36,39,40,50]. If we assume that water and small molecules moved from brain surface across the dialysis membrane into the osmotic chamber, and that the acute brain injury is associated with persistently leaky blood vessels during the experimental period, we speculate that our failure to detect a reduction in the water content reflects an insensitivity in the assay, perhaps related to the dissection.

Using the same apparatus, we showed that cooling of the dialysate is associated with local cooling of brain. Local cooling of brain has been achieved in several different ways[4,6,8,23,46,52]. These include: ChillerPad and ChillerStrip system (Seacoast Technologies, Neurosurgical device for thermal therapy U.S. Pat. No. 6,648,907)[52]; insertion of a metal coil over the skull[8]; application of a thermoelectric (Peltier) chip to the brain surface[23]; placement of a catheter with cooled fluid on the brain surface[6]; endovascular perfusion with cooled fluids[46]. Experimental studies show that reduction of body (and therefore brain) temperature from normal (37° C.) to 32° C. is protective against a variety of brain injuries. This temperature can easily be achieved by cooling the reservoir or the delivery tubing of the dialysate from room temperature to <20° C. using ice baths or refrigerated cooling systems. At these temperatures, the flow characteristics of the dialysis fluids tested thus far is not altered.

Other experimental approaches have been used to reduce edema through local effects on osmotic activity or fluid flow. Intraventricular administration of albumin was of limited use for reducing brain water in rat experiments[24,34]. Multiple stab wounds through the cortex seemed to facilitate movement of edema fluid[7]. Tissue dialysis using multiple needle insertion seems to do the same[48,49]. All of these involve insertion of devices into the already damaged brain. These have the potential for causing further bleeding. Our experiment provides evidence that dialysis across the brain surface can reduce brain edema and intracranial pressure in a minimally invasive manner. Following traumatic or ischemic brain damage with severe localized swelling, large craniotomies are sometimes performed in humans to relieve the intracranial pressure and allow the brain to swell outward, rather than causing intracranial herniation[13,14,47]. An osmotic cell may be applied to the brain surface to dialyze and cool the brain with minimal additional risk in this circumstance.

Results of Experimental Studies on Freeze Injured Rat Brain

Six rats died within 30 minutes of cryogenic brain injury and were not used for subsequent dialysis experiments. In the pilot experiments, histological evaluation showed that uninjured brain surface subjected to dialysis for 2 hours (n=3) exhibited no abnormality (e.g. shrunken neurons or inflammation). Water content in uninjured brain subjected to dialysis (n=3; 77.1±0.2%) and intact brain (n=3; 76.4±0.2%) did not differ. Brains subjected to cryo-injury alone (n=3) or to cryo-injury with dialysis (n=3) had a tapered column of damaged brain tissue that was broadest at the brain surface. In vivo, the brain surface appeared swollen and reddish. Histologically, the tissue exhibited diminished staining intensity due to edema and foci of hemorrhage especially at the periphery and depths of the lesion, which usually approached the deep white matter.

Figure 3:
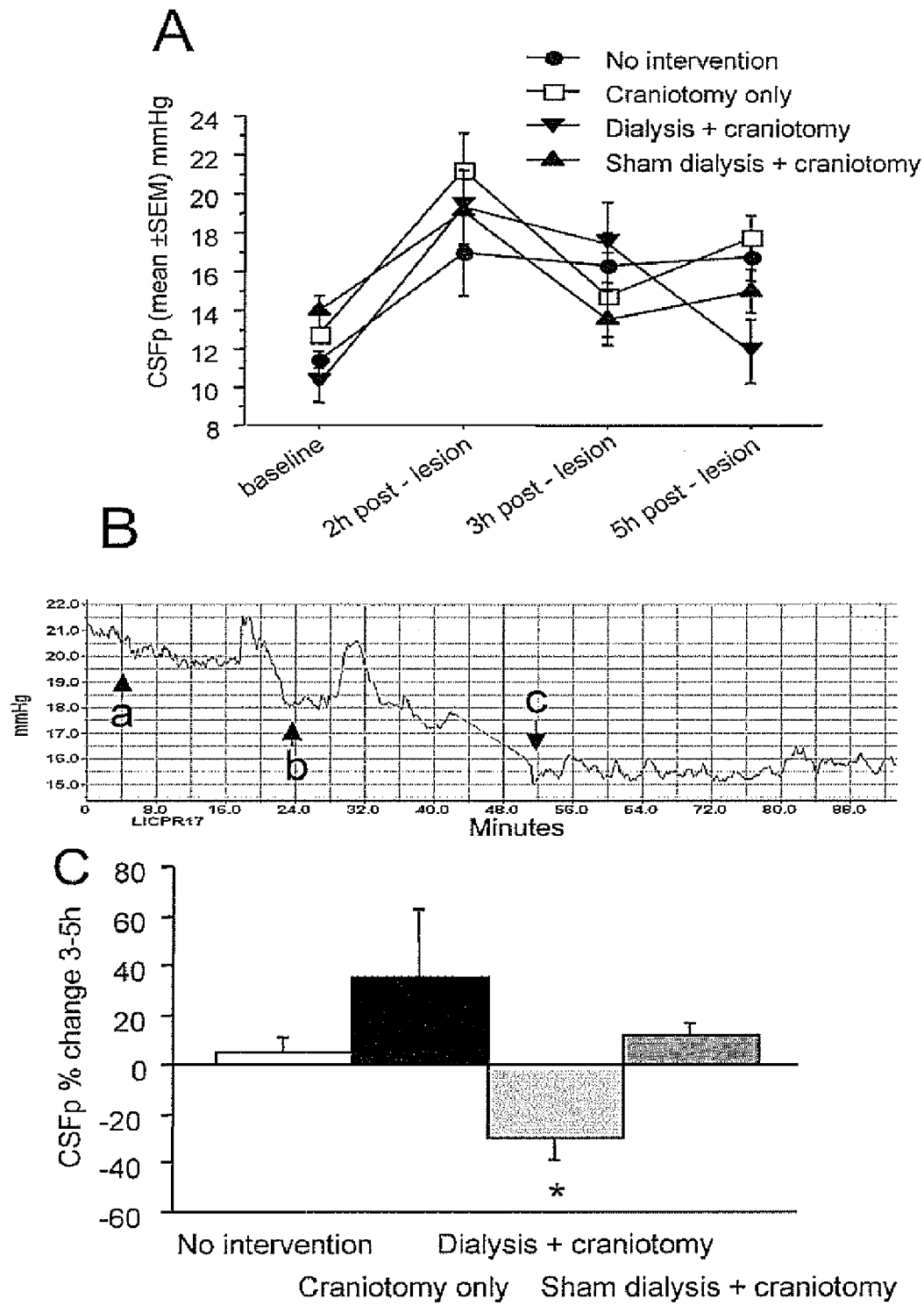
FIG. 3. A. Line graph showing mean (±SEM) CSF pressure, which reflects ICP, at different times in the experiment. The rat brains were injured by localized freezing and dialysis was performed for 2 hours, beginning 1 hour after freezing. The dialysis fluid used was a 15% solution of 15000 molecular weight dextran and the semipermeable membrane had a pore size of 3500. The group subjected to dialysis showed decreasing CSF pressure, while other groups had stable or increasing pressure. B. Sample tracing of CSF pressure from a rat at the start of dialysis (a) showing the decrease in pressure. Note that a stable pressure is reached after ~50 minutes (b). C. Bar graph showing percentage change in CSF pressure during the 2-hour period of dialysis and comparable times in other groups (mean±SEM). The negative change in pressure in the dialysis group was significantly greater (*) in comparison to the craniotomy only group (p=0.0061) and tended to be greater than the sham dialysis group (p=0.06).
Figure 4:
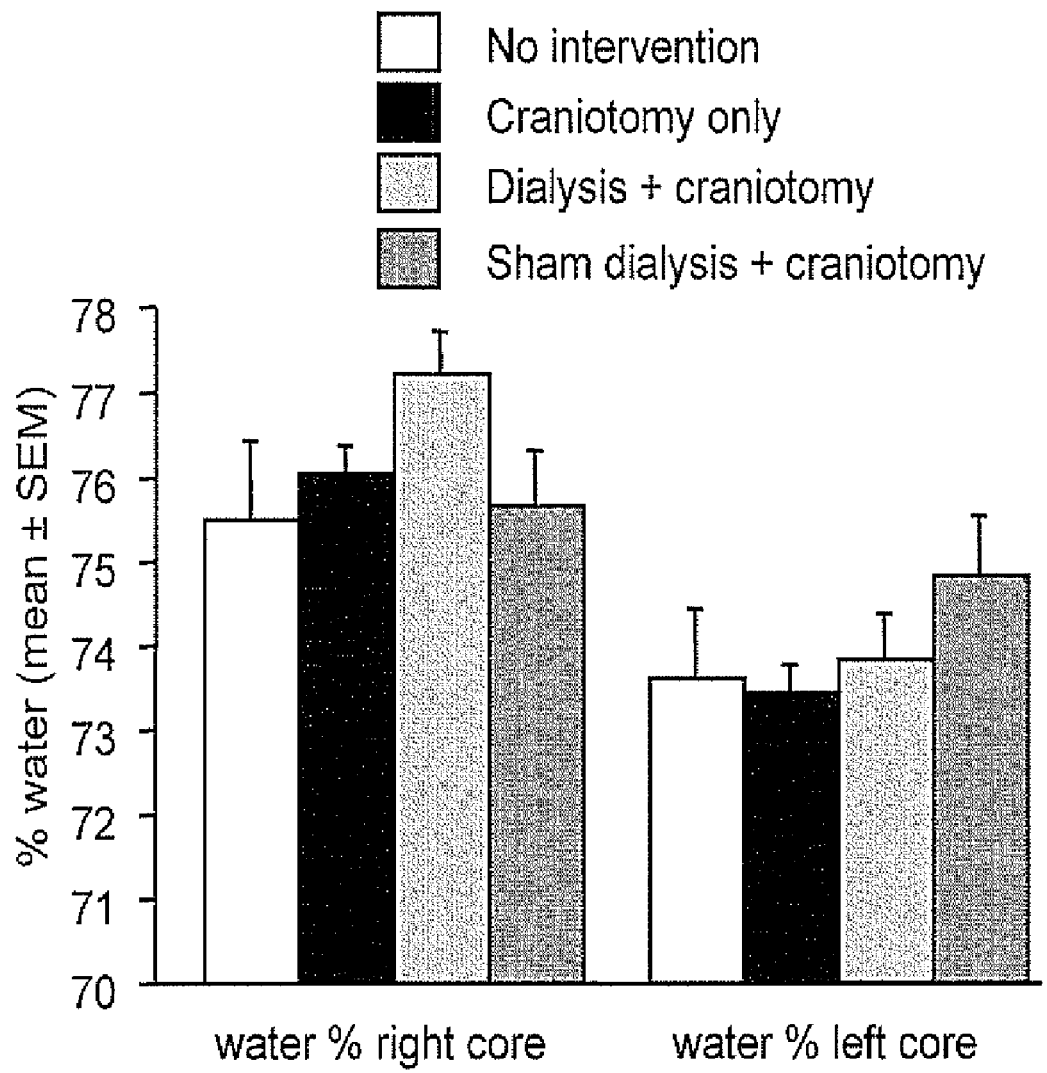
FIG. 4. Bar graph showing percent water content in core sample of cerebrum from lesioned/dialyzed right side of brain and control left side. There is no significant difference between groups.

In the randomized pressure monitoring experiment, CSF pressure increased significantly from baseline in all groups after cryo-injury, and tended to decrease slightly after craniectomy. Rats subjected to dialysis for 2 hours (group 4) had decreasing ICP while other groups had stable or increasing CSF pressure (FIG. 3). The groups were significantly different (repeated measures ANOVA; F=3.064, p=0.0056, Lambda=27.578). The CSF pressure percentage decrease was significantly greater in the dialysis group, whereas the sham dialysis showed no difference in comparison to craniotomy alone (FIG. 3C). The injured right cerebrum had higher water content than the intact left cerebrum. However, dialysis was not associated with reduced water content despite dropping CSF pressure (FIG. 4). This was somewhat surprising because we expected the water content to be lowered. The next experiment (following paragraph) shows that the flow of edema fluid is reversed. Consequently, the damaged brain sampled for water content analysis is in a steady state, but the surrounding tissues differ with respect to flow of the edema fluid.

Figure 5:
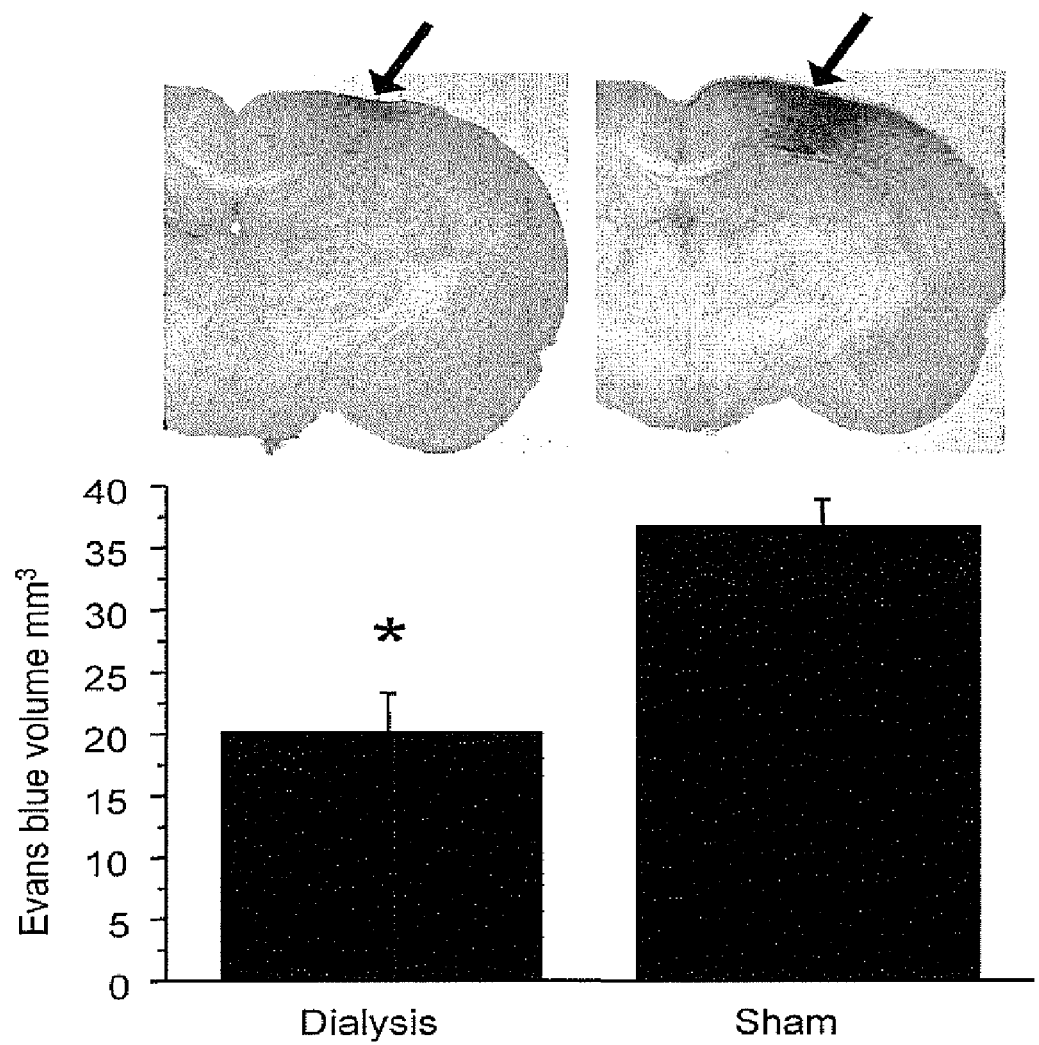
FIG. 5. Bar graph showing the reduction in spread of edema fluid through rat brain, as measured by Evans blue-albumin distribution. Rats received intravenous Evans blue tracer one hour prior to freezing brain injury. Dialysis (or sham dialysis) was started 1 hour later and continued for 4 hours. Then rat brains were removed and sliced to assess the spread of the brain tracer. In sham dialyzed rats, edema fluid moves to the depths of the brain where it is retained. In dialyzed rats, edema fluid moves toward the outer surface of the brain and is removed by the dialysis system.

Following intravenous injection of Evans blue the sclera, lips, paws and injured brain surface turned blue. During the randomized 4-hour dialysis (15% dextran) or sham dialysis period, body temperature and respiration remained stable. After dialysis but not sham dialysis, some of the rats had a sunken rather than raised brain surface at the site of the cryogenic lesion. This indicates that the brain swelling had been prevented. Coronal sections through the brain showed blue coloration in the cortex at the site of the lesion and extending up to 3 mm deep into the hippocampus as well as laterally along the external capsule and medially across the corpus callosum. Rats with sham dialysis had blue coloration in 36.8±2.1 mm$^3$ brain and rats with 15% dextran dialysis had blue coloration in 19.9±3.3 mm$^3$ brain (p=0.0008, unpaired t test) (FIG. 5). Inulin solution (10%) was more difficult to work with because it tended to precipitate. Pentastarch solution (10%) appeared to work almost as well as dextran.

Figure 6:
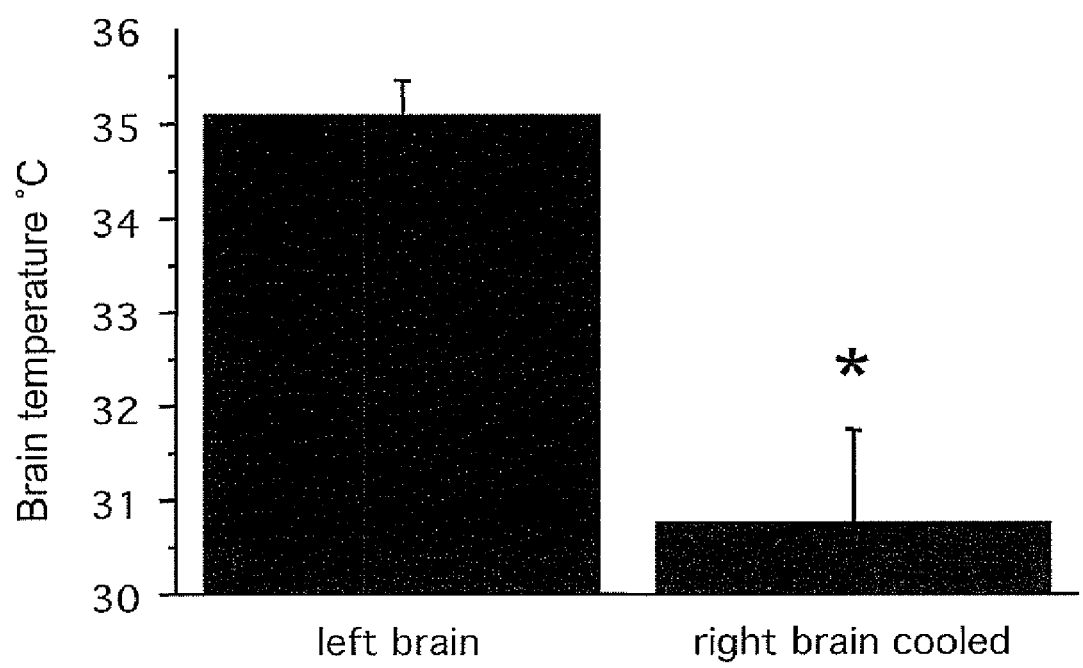
FIG. 6. Bar graph showing brain temperature near the site of the dialysis chamber contact. The inflow fluid is cooled by passing loops of tubing through an ice bath; the length of cooled tubing determines the temperature in the dialysis chamber. Cooling of the dialysate caused local cooling of the brain tissue.

We then showed that chilled dialysate (15% dextran) could provide local brain cooling. The baseline osmotic chamber temperature was 23.6±0.2° C. and it decreased to 18.4±0.4° C. (p<0.0001, one tailed paired t test). Cooling the dialysate created a left to right temperature gradient (35.1±0.4 vs. 30.7±1.0° C.; p=0.0024, one tailed paired t test) (FIG. 6).

Materials and Methods for Rat Experiments

Osmotic Flow Cell Fabrication and Dialysate

An osmotic flow cell was constructed from an acrylic sample tube, bell shaped at one end (Micro Osmometer Model 3300, Advanced Instruments Inc., MA, USA). It was modified by connecting inflow (3 mm inner diameter) and outflow (1 mm inner diameter) channels equipped with a 3-way stopcock. Regenerated cellulose semipermeable membrane with nominal pore size of 3500 D (Pierce Snakeskin® Dialysis Tubing) was soaked in distilled water then connected to the sampler using a silicone ring (FIG. 1). The volume of the osmotic cell is 1.0 mm$^3$, and the membrane contact area is 50.2 mm$^2$.

The osmolality of plasma, ISF, and CSF are roughly equivalent under normal conditions[10], although the protein content of plasma is much higher. Following experimental brain damage, the colloid osmotic pressure of brain ISF approaches that of plasma for at least 5 hours[16,33], and CSF osmolarity in the rat brain freeze injury model of vasogenic brain edema increased from 277±31 mOsm/L H$_2$O to 348±108 mOsm/L H$_2$O within 4 hours[34]. Protein content contributes to delayed resolution of edema fluid[17]. We made artificial cerebrospinal fluid (aCSF) (final ion concentration in mM: Na 150; K 3.0; Ca 1.4; Mg 0.8; P 1.0; Cl 155)[10]. The osmolarity measured using the freezing point depression technique (Micro Osmometer Model 3300, Advanced Instruments Inc.) was 289±3 mOsm/L H$_2$O. Rat lumbar CSF osmolarity (n=20) was 302±3 mOsm/kg H$_2$O. To create an osmotic gradient for brain dialysis we added colloidal Dextran with molecular weight 15,000-20,000 D (Sigma-Aldrich, Inc., MO, USA) to aCSF (15% W/V) to create a perfusate (aCSF-D15%) with osmolality 392±3 mOsm/L H$_2$O and pH 6.62±0.3. To test the apparatus in vitro, the osmotic cell was filled with 1 mL aCSF-D15 then immersed in a Petri dish filled with aCSF at room temperature. Equilibrium was reached in ~15-20 minutes. For the in vivo experiments, to ensure continuous exchange of the dialysate, the osmotic cell was connected to an intravenous infusion set and flow was controlled by drip rate at approximately 0.6 ml/min.

Animals, Anesthesia, Pressure Catheter Insertion

Twenty young adult male Sprague-Dawley rats (350-370 g) were maintained on a 12 hours light/dark cycle with ad libitum access to tap water and standard food. Spontaneously breathing rats were anesthetized with 1.5% isoflurane in oxygen, and subjected to implantation of a telemetric pressure transmitter (TL11M2-C50-PXT, Data Sciences Intl.) into the lumbar CSF space. A midline skin incision along the spinous processes L4-6 was made and spinous process and lamina L5 were exposed using a surgical microscope, partial laminectomy L5 was made, and the dura mater and arachnoid membrane were opened. CSF was collected with 20 µl Advanced Ease-Eject Sampler (Advanced Instruments Inc., MA) and CSF osmolality measured (as described above). The pressure catheter (0.4 mm outer diameter) was inserted into the subarachnoid space of L5 and advanced 10 mm. The spinal defect was closed with drop of cyanoacrylate—Vet Bond glue. The transducer was placed in a skin pouch through the same incision and the wound was closed with surgical suture. The system response to pressure change was tested by manual abdominal compression. The rats were allowed to recover for 24-48 hours postoperatively.

Experimental Brain Injury and Treatment

Focal freezing was used to create a necrotic lesion with vasogenic edema[28]. Spontaneously breathing rats were anesthetized with 1.5% isoflurane in oxygen and the scalp was opened in the midline. Cryogenic bran injury was created by applying a copper rod (3 mm diameter, cooled in liquid nitrogen) to the skull (centered 4 mm posterior to bregma and 4 mm lateral to midline) for 60 seconds. The wound was closed with Michel clips. To reduce pain after injury, buprenorphine 0.05 mg/kg was injected subcutaneously. Lumbar ICP was continuously recorded prior to, during, and after the lesion. In pilot experiments using 15 rats, normal rats and rats with cryo-injury underwent brain surface dialysis for 2 hours (as described below) followed by perfusion fixation to ascertain the response of the brain surface to the dialysis membrane. These were compared to rats with cryo-injury alone. A separate set of normal rats had water content measured in brain after 2 hours dialysis.

At the beginning of the experiment, 20 unmarked envelopes containing assignments to 4 treatment groups were prepared. Immediately after cryo-injury, an envelope was chosen randomly from a container to assign each rat to one of the following experimental groups:

Group 1 (n=5): no treatment, sacrificed 5 hours after cryo-injury.

Group 2 (n=5): decompressive craniectomy 2 hours after cryo-injury and sacrificed 5 hours after cryo-injury.

Group 3 (n=5): decompressive craniectomy 2 hours after cryo-injury followed by sham brain dialysis. Under isoflurane anesthesia with the head secured in a stereotactic frame, an empty osmotic cell was positioned in contact with damaged brain surface for 2 hours. The rats were sacrificed 5 hours after cryo-injury.

Group 4 (n=5): decompressive craniectomy 2 hours after cryo-injury followed by brain dialysis. As in group 3 except the osmotic cell was perfused with aCSF-D15 and the brain surface was dialyzed for 2 hours. The rats were sacrificed 5 hours after cryo-injury.

Figure 2:
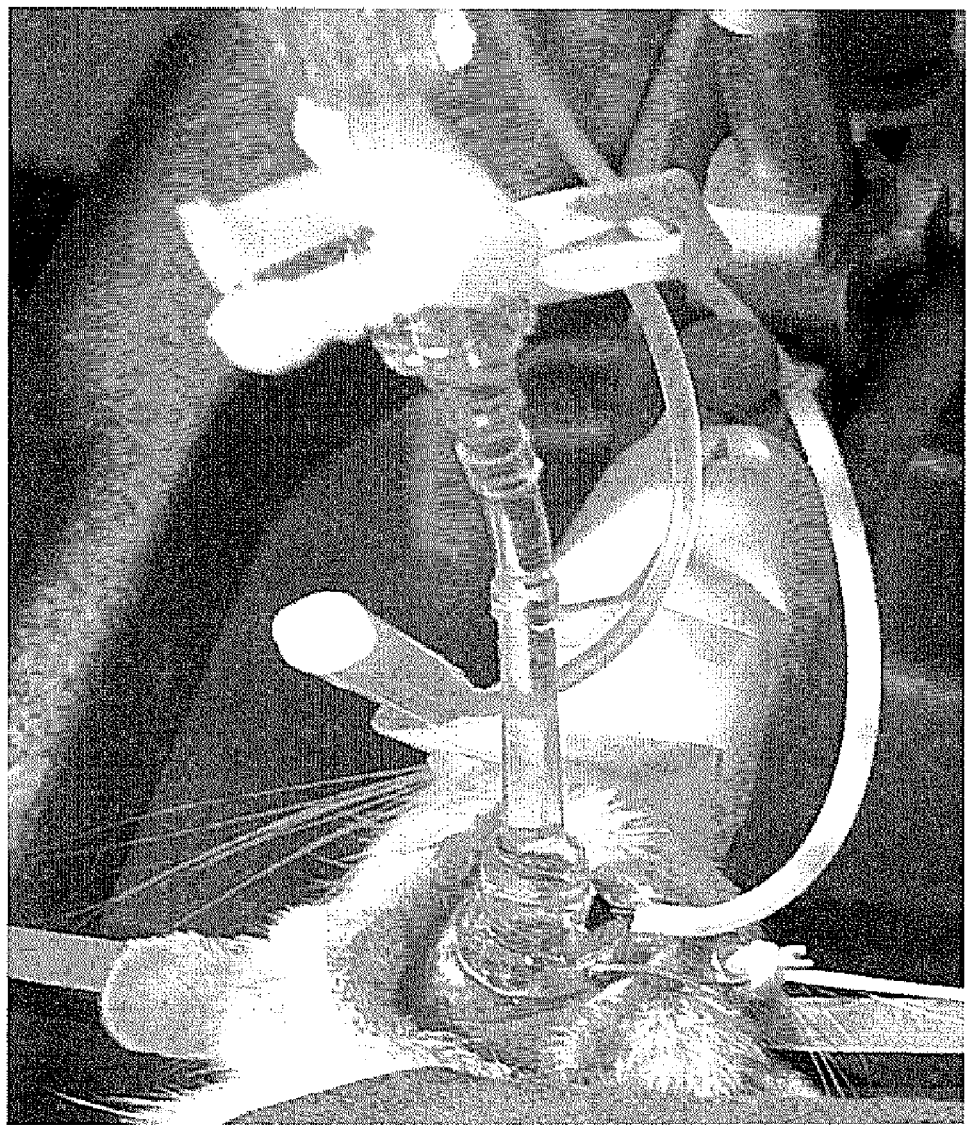
FIG. 2. Photograph showing experimental osmotic cell applied to the surface of a rat brain. The head is held in a stereotactic frame and the snout is covered by the anesthetic delivery cone.

Decompressive craniectomy was performed 2 hours after cryo-injury. Rats were anesthetized with 1.5% isoflurane in oxygen, scalp clips were removed, the periosteum was dissected to the right parieto-temporal skull ridge, four 2 mm holes were drilled while irrigating with normal saline, and a right parieto-temporal decompressive craniectomy 5.5×10 mm was created with a small rongeur. The meninges were opened using a surgical microscope for magnification. Rats were placed on warming blanket with a rectal probe to maintain the body temperature at 37° C., and the head was positioned in a stereotactic head holder (David Kopf Instruments, Tujunga, Calif.). In group 2, the scalp was closed. In groups 3 and 4 the osmotic cell was applied to the damaged brain surface and held in place with a clamp secured to the head frame (FIG. 2). Lumbar CSF pressure data were collected (1 sample per 10 seconds) and sent telemetrically via the Data Exchange Matrix and continuously analyzed (Dataquest A.R.T.™ Version 3.01 system, Data Sciences International, MN, USA). For intergroup comparisons we determined the mean pressure during a 10 minute time block at the following four time points: baseline prior to cryo-injury under anesthesia; 2 hours after cryo-injury (prior to craniectomy in groups 2, 3, 4 and in awake rats from group 1); 3 hours after cryo-injury (1 hour after craniectomy in anesthetized rats from groups 2, 3, 4 and in awake rats from group 1); 5 hours after cryo-injury immediately prior to sacrifice in anesthetized rats (after 2 hours dialysis or sham dialysis in groups 4 and 3 respectively).

Brain Sampling and Quantitation of Brain Edema

All rats were sacrificed 5 hours after cryo-injury by barbiturate overdose. We did not perfusion flush the vasculature because we were concerned that it could alter the water content in damaged brain. Equal volume (62.8 mm$^3$) brain cores were sampled from site of cryo-injury and contralateral mirror area (centered 4 mm posterior to bregma, 4 mm lateral to midline) with a cylindrical punch sampler (4 mm inner diameter×5 mm height)[12] by a person blinded to the nature of the prior intervention. Weight of wet and subsequently dried (2-3 days at 100° C.) brain tissue specimens was measured and the percentage water content was calculated. Feasibility experiments were also conducted using other dialysates including 10% inulin and Pentaspan.

Evaluation of Edema Spread

In a separate group of 12 rats young adult SD rats (250-350 g) the dialysis experiment was repeated but for a longer period to determine if movement of interstitial fluid was altered. On Day 1 the lumber CSF pressure monitor was implanted and the rats were allowed to recover overnight. On Day 2 a cryogenic brain injury was created as above. Thirty minutes later, Evans blue (0.5 ml of 1% solution) was injected into the femoral vein. Sixty minutes later the craniectomy was performed. After craniotomy the rats were randomly assigned to dialysis or sham treatment (prelabeled assignment sheets were blindly chosen from an envelope. The dialysis module was applied to the brain surface and, beginning 2 hours after the cryogenic lesion and continuing for 4 hours, dialysis (15% dextran) or sham dialysis (wetted dialysis membrane with empty chamber) was performed. The rats were killed at the end of the dialysis by overdose with $CO_2$ followed by transcardiac perfusion with 10% formalin. The head was removed and placed in the same fixative overnight. Then the brain was removed and placed in a steel slicing guide and cut into 1 mm thick coronal slices. Brain edema fluid appeared blue. The brain slices were photographed then the slices nearest center of lesion were embedded in paraffin for histologic analysis. Using an image analysis system (NIH ImageJ) the area of blue discoloration and the total area of brain slice were measured and the total volume of edema spread was calculated.

Using this protocol, feasibility experiments were conducted using osmotic cells constructed with dialysis membranes with pore size of 7000 D (Pierce Snakeskin Dialysis Tubing from regenerated cellulose) (1 rat dialyzed with 15% dextran). Other dialysates were tested with the 3500 D dialysis membrane including 10% inulin (1 rat; 368 mOsm/L; Sigma) and 10% pentastarch (average MW 265,000 D) in 0.9% sodium chloride (2 rats; 338 mOsm/L; Pentaspan®, Dupont Pharmaceuticals, Wilmington Del.). Other forms of hydroxyethyl starch have been shown to be effective osmotic agents in experimental peritoneal dialysis[18].

Measurement of Brain Temperature

To assess the ability of the surface dialysis device to simultaneously cool the brain, the following experiment was conducted. Six normal rats anesthetized with 1.5% isoflurane in oxygen and positioned in the head holder. They underwent right side craniectomy for application of the dialysis module to the brain surface. In addition, a 3 mm hole was drilled over the left parietal lobe. Wire thermistors were inserted bilaterally, 1.5 mm below the brain surface; on the right side this was under the dialysis module. Temperature was recorded simultaneously in the right and left cerebrum as well as in the dialysis chamber. Dialysate (15% dextran solution) was perfused through the chamber at a rate of 2.4 ml/minute at room temperature (23-24° C.) for two hours and then switched to a chilled (5-7° C.) solution running through the chamber at a maximum rate of ~20 ml/minute for up to 2 hours.

Statistical Analysis

Data are expressed as mean±standard error of mean. Differences between measured CSF pressure and water content were tested for significance with repeated measures ANOVA followed Fisher's least square difference test for equal groups. Correlation analysis (Fisher r to z test) was applied to determine the relationship between final CSF pressure and injured brain water content. Area of edema spread was compared between the two groups using Student's t test (two tailed). Temperature measurements were compared using one-tailed paired t tests.

The methods and devices described herein differ from the prior art. First, the instant method takes advantage of the fact that brain surface membranes are potentially permeable to water. Application of the dialysis process to the brain surface rather than via penetrating needles is inherently less invasive and therefore does not damage the brain further. Second, application of a sheet of semipermeable material to the brain surface offers a larger surface area for dialysis and therefore can remove more water. Third, the use of a larger volume chamber allows more rapid flow of dialysate fluid, which can be cooled thereby offering the potential for local cooling of brain tissue precisely in the injured area, as discussed herein.

While the preferred embodiments of the invention have been described above, it will be recognized and understood that various modifications may be made therein, and the appended claims are intended to cover all such modifications which may fall within the spirit and scope of the invention.

REFERENCES

1. Abbott N J: Evidence for bulk flow of brain interstitial fluid: significance for physiology and pathology. Neurochem Int 45:545-552, 2004
2. Alcolado R, Weller R O, Parrish E P, et al: The cranial arachnoid and pia mater in man: anatomical and ultrastructural observations. Neuropathol Appl Neurobiol 14:1-17, 1988
3. Angelov D N: Ultrastructural investigation of the meningeal compartment of the blood-cerebrospinal fluid-barrier in rats and cats. A horseradish peroxidase study. Z Mikrosk Anat Forsch 104:1-16, 1990
4. Bakken H E, Kawasaki H, Oya H, et al: A device for cooling localized regions of human cerebral cortex. Technical note. J Neurosurg 99:604-608, 2003
5. Bhardwaj A, Ulatowski J A: Hypertonic saline solutions in brain injury. Curr Opin Crit Care 10:126-131, 2004
6. Cheng H, Shi J, Zhang L, et al: Epidural cooling for selective brain hypothermia in porcine model. Acta Neurochir (Wien) 148:559-564, 2006
7. Chiou T L, Chiang Y H, Song W S, et al: Transdural cortical stabbing facilitates the drainage of edema fluid out of cold-injured brain. Acta Neurochir Suppl (Wien) 60:459-461, 1994
8. Clark D L, Colbourne F: A simple method to induce focal brain hypothermia in rats. J Cereb Blood Flow Metab 27:115-122, 2007
9. Corbett D, Nurse S: The problem of assessing effective neuroprotection in experimental cerebral ischemia. Prog. Neurobiol. 54:531-548, 1998
10. Davson H, Segal M B: Physiology of the CSF and Blood-Brain Barriers. Boca Raton: CRC Press, 1996
11. Del Bigio M R: Glial linings of the brain, in Walz W (ed): The Neuronal Environment: Brain Homeostasis in Health and Disease. Totowa N.J.: Humana Press Inc., 20021 pp 341-375
12. Del Bigio M R, Bruni J E: Cerebral water content in silicone oil-induced hydrocephalic rabbits. Pediatr Neurosci 13:72-77, 1987
13. Els T, Oehm E, Voigt S, et al: Safety and therapeutical benefit of hemicraniectomy combined with mild hypothermia in comparison with hemicraniectomy alone in patients with malignant ischemic stroke. Cerebrovasc Dis 21:79-85, 2006
14. Els T, Oehm E, Voigt S, et al: Safety and Therapeutical Benefit of Hemicraniectomy Combined with Mild Hypothermia in Comparison with Hemicraniectomy Alone in Patients with Malignant Ischemic Stroke. Cerebrovasc Dis 21:79-85, 2005
15. Flanigan M: Dialysate composition and hemodialysis hypertension. Semin Dial 17:279-283, 2004
16. Gazendam J, Go K G, van Zanten A K: Composition of isolated edema fluid in cold-induced brain edema. J. Neurosurg. 51:70-77, 1979
17. Groeger U, Marmarou A: The importance of protein content in the oedema fluid for the resolution of brain oedema. Acta Neurochir 101:134-140, 1989
18. Hain H, Schutte W, Pustelnik A, et al: Ultrafiltration and absorption characteristics of hydroxyethylstarch and dextran during long dwell peritoneal dialysis exchanges in rats. Adv Perit Dial 5:28-30, 1989
19. Hattori H, Kimura M, Takahashi M, et al: Morphological estimation of brain extracellular fluid dynamics in cold-induced edema from the aspect of cerebrospinal fluid-extracellular fluid communication. Acta Pathol Jpn 40:314-321, 1990
20. Hillman J, Aneman O, Anderson C, et al: A microdialysis technique for routine measurement of macromolecules in the injured human brain. Neurosurgery 56:1264-1270, 2005
21. Hutchinson P, Timofeev I, Kirkpatrick P: Surgery for brain edema. Neurosurg Focus 22:E14, 2007
22. Ikeda Y, Wang M, Nakazawa S: Simple quantitative evaluation of blood-brain barrier disruption in vasogenic brain edema. Acta Neurochir Suppl (Wien) 60:119-120, 1994
23. Imoto H, Fujii M, Uchiyama J, et al: Use of a Peltier chip with a newly devised local brain-cooling system for neocortical seizures in the rat. Technical note. J Neurosurg 104:150-156, 2006
24. Is M, Uzan M, Unal F, et al: Intraventricular albumin: an optional agent in experimental post-traumatic brain edema. Neurol Res 27:67-72, 2005
25. Kaufmann A M, Cardoso E R: Aggravation of vasogenic cerebral edema by multiple-dose mannitol. J Neurosurg 77:584-589, 1992
26. Kawamata T, Mori T, Sato S, et al: Tissue hyperosmolality and brain edema in cerebral contusion. Neurosurg Focus 22:E5, 2007
27. Kimelberg H K: Water homeostasis in the brain: basic concepts. Neuroscience 129:851-860, 2004
28. Klatzo I, Piraux A, Laskowski E J The relationship between edema, blood-brain-barrier and tissue elements in a local brain injury. J. Neuropathol. Exp. Neurol. 17:548-564, 1958
29. Leslie R A, MacDonald L T, Love J A: The permeability to exogenous protein of the wall of the superior sagittal sinus of the cat, Brain Res Bull 11:547-554, 1983

30. Levin E, Sisson W B: The penetration of radiolabeled substances into rabbit brain from subarachnoid space. Brain Res 41:145-153, 1972
31. Marmarou A: A review of progress in understanding the pathophysiology and treatment of brain edema. Neurosurg Focus 22:E1, 2007
32. Morley N C, Berge E, Cruz-Flores S, et al: Surgical decompression for cerebral oedema in acute ischaemic stroke. Cochrane Database Syst Rev:CD003435, 2002
33. Odland R M, Sutton R L: Hyperosmosis of cerebral injury. Neurol Res 21:500-508, 1999
34. Onal C, Unal F, Turantan M I, et al: The effect of intraventricular albumin in experimental brain oedema. Acta Neurochir (Wien) 139:661-668, 1997
35. Perez-Gomez J, Bindslev N, Orkand P M, et al: Electrical properties and structure of the frog arachnoid membrane. J Neurobiol 7:259-270, 1976
36. Proescholdt M G, Hutto B, Brady L S, et al: Studies of cerebrospinal fluid flow and penetration into brain following lateral ventricle and cisterna magna injections of the tracer [14C]inulin in rat. Neuroscience 95:577-592, 2000
37. Rabinstein A A: Treatment of cerebral edema. Neurologist 12:59-73, 2006
38. Raslan A, Bhardwaj A: Medical management of cerebral edema. Neurosurg Focus 22:E12, 2007
39. Reulen H J, Graham R, Spatz M, et al: Role of pressure gradients and bulk flow in dynamics of vasogenic brain edema. J Neurosurg 46:24-35, 1977
40. Reulen H J, Tsuyumu M, Tack A, et al: Clearance of edema fluid into cerebrospinal fluid. A mechanism for resolution of vasogenic brain edema. J Neurosurg 48:754-764, 1978
41. Rieth K G, Fujiwara K, Di Chiro G, et al: Serial measurements of CT attenuation and specific gravity in experimental cerebral edema. Radiology 135:343-348, 1980
42. Roberts I: Barbiturates for acute traumatic brain injury. Cochrane Database Syst Rev:CD000033, 2000
43. Sadanaga K K, Ohnishi S T: Studies on the permeability of potassium ions across the dura and arachnoid mater of the rat spinal cord. J Neurotrauma 7:257-266, 1990
44. Sahuquillo J, Arikan F: Decompressive craniectomy for the treatment of refractory high intracranial pressure in traumatic brain injury. Cochrane Database Syst Rev: CD003983, 2006
45. Schneider G H, Hennig S, Lanksch W R, et al: Dynamics of posttraumatic brain swelling following a cryogenic injury in rats. Acta Neurochir Suppl (Wien) 60:437-439, 1994
46. Slotboom J, Kiefer C, Brekenfeld C, et al: Locally induced hypothermia for treatment of acute ischaemic stroke: a physical feasibility study. Neuroradiology 46:923-934, 2004
47. Subramaniam S, Hill M D: Massive cerebral infarction. Neurologist 11:150-160, 2005
48. Sutton R L, Quist H, Mathews W, et al: Further evidence that tissue ultrafiltration reduces experimental cerebral edema, in Society for Neuroscience, 2000, Vol 26, p abstract #279.277
49. Sutton R L, Quist H, Mathews W, et al: Ultrafiltration reduces cerebral edema after traumatic brain injury in rat, in Society for Neuroscience, 1999, Vol 25, p 313 (abstract #127.318)
50. Tsuyumu M, Reulen H J, Prioleau G: Dynamics of formation and resolution of vasogenic brain oedema. I. Measurement of oedema clearance into ventricular CSF. Acta Neurochir (Wien) 57:1-13, 1981
51. Unterberg A W, Stover J, Kress B, et al: Edema and brain trauma. Neuroscience 129:1019-1027, 2004
52. Wagner K R, Beiler S, Beiler C, et al: Delayed profound local brain hypothermia markedly reduces interleukin-1 beta gene expression and vasogenic edema development in a porcine model of intracerebral hemorrhage. Acta Neurochir Suppl 96:177-182, 2006
53. Wakai A, Roberts I, Schierhout G. Mannitol for acute traumatic brain injury. Cochrane Database Syst Rev: CD001049, 2005
54. Wright P M, Nogueira G J, Levin E: Role of the pia mater in the transfer of substances in and out of the cerebrospinal fluid. Exp Brain Res 113:294-305, 1971

The invention claimed is:

1. A method of treating brain swelling comprising:
opening the skull a patient of a patient who has suffered or is suspected of having suffered an injurious event sufficient to induce swelling of the brain;
inserting an osmotic cell into a dural opening or under a dural flap onto a brain, said osmotic cell comprising:
an osmotic cell body comprising an inner chamber for retaining a solution therein;
a semi-permeable membrane for contacting the brain;
an inflow port; and
an outflow port;
closing the scalp of the patient over the osmotic cell such that pressure from the scalp holds the osmotic cell in place; and
flowing a solution having an osmolarity greater than that of fluid in the extracellular compartment of the brain through the inflow port, into the inner chamber, past the semi-permeable membrane and out of the inner chamber through the outflow port such that interstitial fluid from the brain proximal to the semi-permeable membrane osmotically flows across the membrane and into the inner chamber of the body.

2. The method according to claim 1 wherein the solution is at a temperature arranged to lower the temperature of the brain to a temperature below body temperature.

3. The method according to claim 1 wherein the solution is chilled to a temperature below room temperature.

4. The method according to claim 1 wherein the solution further comprises a medicinal agent selected from the group consisting of an antibiotic, a neuroprotective agent or a neuroregenerative agent.

* * * * *